United States Patent [19]

Brumley et al.

[11] 4,163,845
[45] Aug. 7, 1979

[54] RECYCLE OF SPENT ACID IN NITROLYSIS OF HEXAMINE TO RDX

[75] Inventors: Charles D. Brumley, Greeneville; John M. Staples, Kingsport, both of Tenn.

[73] Assignee: The United States of America as represented by the Secretary of the Army, Washington, D.C.

[21] Appl. No.: 900,212

[22] Filed: Apr. 26, 1978

[51] Int. Cl.$^2$ ............................................. C07D 251/06
[52] U.S. Cl. ............................... 544/215; 260/239 HM
[58] Field of Search .................. 544/215; 260/239 HM

[56] References Cited

U.S. PATENT DOCUMENTS

| | | | |
|---|---|---|---|
| 2,485,855 | 10/1949 | Blomquist et al. | 544/215 |
| 2,900,381 | 8/1959 | Thatcher | 544/215 |
| 3,351,585 | 11/1967 | Lee et al. | 544/215 |
| 3,676,425 | 7/1972 | Dawson et al. | 260/239 HM |

Primary Examiner—John M. Ford
Attorney, Agent, or Firm—Nathan Edelberg; Harold H. Card, Jr.; A. Victor Erkkila

[57] ABSTRACT

Recycle of spent acid in nitrolysis of hexamine to RDX is accomplished under conditions, which avoid or minimize the need to process the spent acid through conventional costly recovery operations and result in little, if any, reduction of RDX yield. The conditions include (a) effecting the simmering in spent acid containing between 0% and 2% water;

(b) recycling at least part of the spent acid of 0–2% water content to dissolve the hexamine reactant; and (c) preferably also recycling a part of the spent acid, after elimination of any water contained therein with acetic anhydride, to the heel to which the reactants are added in the nitrolysis of hexamine to RDX.

6 Claims, 1 Drawing Figure

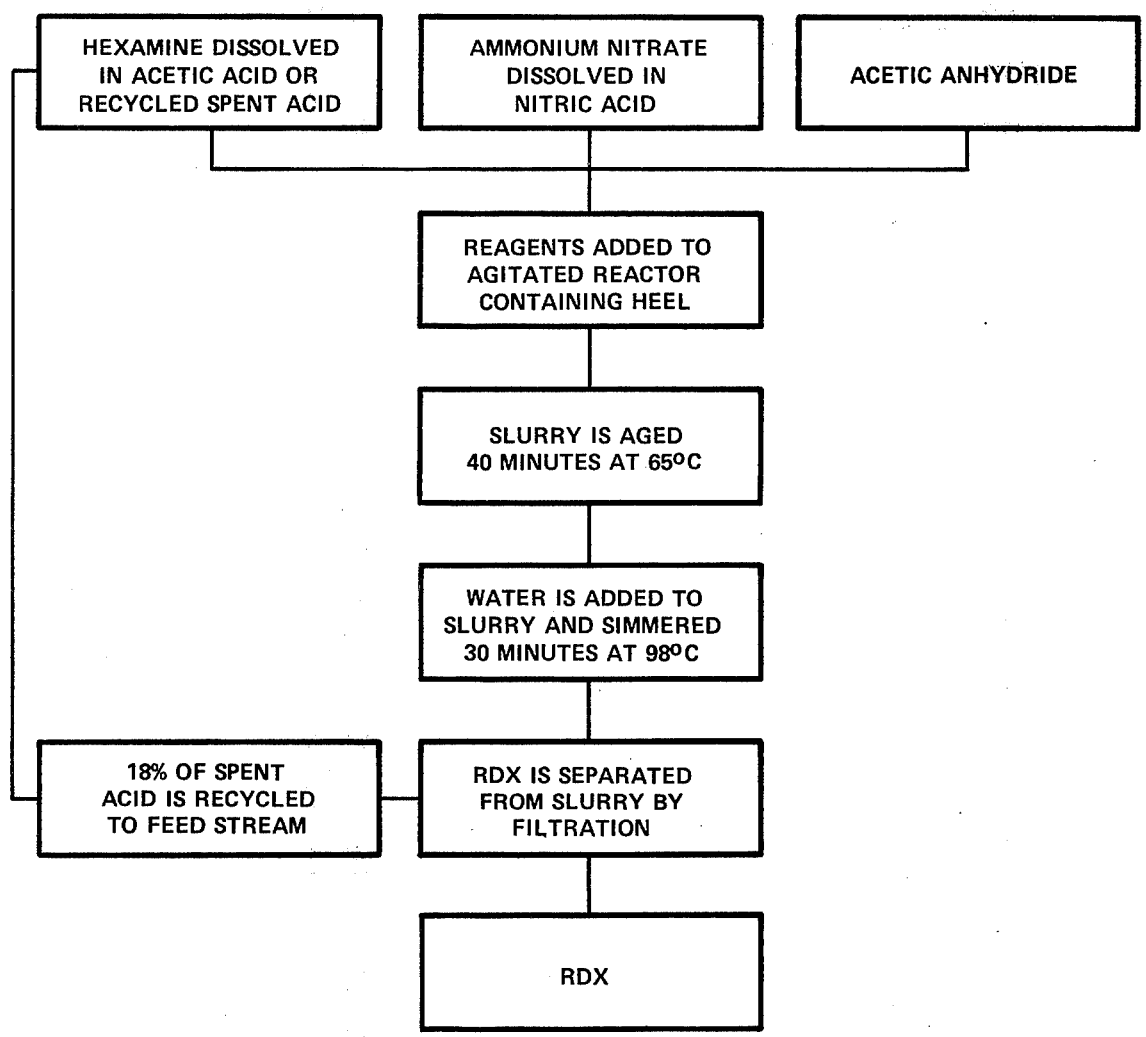

RECYCLE OF SPENT ACID IN NITROLYSIS OF HEXAMINE TO RDX

BACKGROUND OF THE INVENTION 1,3,5-trinitro-1,3,5-triazacyclohexane (RDX) is a high explosive of great brisance, which is usually produced according to the Bachmann process and variations there of by nitrolysis of hexamethylenetretramine (hexamine) with a solution of ammonium nitrate in concentrated nitric acid in the presence of acetic anhydride according to the following overall equation:

$$C_6H_{12}N_4 + 4HNO_3 + 2NH_4NO_3 + 6(CH_3CO)_2O \rightarrow 2C_3H_6O_6N_6 + 12CH_3COOH$$

The reagents are preferably employed in excess over the stoichiometric proportions of nitric acid, ammonium nitrate and acetic anhydride, and are usually added incrementally to a reactor charged with a heel consisting essentially of acetic acid, which may contain up to a few percent of nitric acid, ammonium nitrate and acetic anhydride.

The nitrolysis of hexamine to RDX according to the Bachmann process yields a slurry of RDX in anhydrous spent acid. Normally, the anhydrous slurry is diluted with water to about 40% water content and simmered to destroy undesirable by-products, notably linear nitramines. The slurry is then cooled and filtered to separate the crude RDX from the spent acid (filtrate). At this point the spent acid contains about 40% water, along with acetic acid, nitric acid, and ammonium nitrate, together with various small amounts of RDX and HMX (1,3,5,7-tetranitro-1,3,5,7-tetraazacyclooctane) and other constituents. The process, as industrially practiced, requires that the total volume of dilute spent acid be processed through the complete recovery system, including costly distillation and other operations, to be reconstituted to acetic acid and acetic anhydride prior to reuse in the manufacture of RDX.

SUMMARY OF THE INVENTION

Significant economic advantages might be realized in the manufacture of RDX by avoiding all unnecessary dilution of the spent acid, producing a more concentrated acid input into the acid recovery system, and by recycling the spent acid to the nitrolysis step without sending it through the complete acid recovery operations.

The present invention is directed to a process for recycling spent acid obtained in the RDX nitrolysis under conditions which are novel and unobvious, particularly since they are critical for the achievement of important advantages over the prior art, as more fully described below.

It has been unexpectedly found according to the present invention that the spent acid can be recycled to the nitrolysis reaction with little, if any, loss of RDX yield, as compared to the standard process, by a novel modification, which comprises:

(1) effecting the simmering operation in spent acid from the nitrolysis reaction, which has been diluted with water to eliminate the acetic anhydride and provide a water content of between 0% and about 2%; and (2) recycling at least part of the spent acid of said 0-2% water content, after separation of the RDX product, to dissolve the hexamine reactant.

PRIOR ART STATEMENT

The following patents are of interest relative to the present invention:

West German Pat. No. 1939541
French Pat. No. 2053804

West German Pat. No. 1939541 and French Pat. No. 2053804, relating to the production of HMX, disclose heating of the reaction mass, after nitrolysis and without dilution with water, to destroy by-products and recycling of the resulting spent acid. However, the French patent distills the spent acid to recover its content of acetic acid, which has been separated from HMX and RDX, while the German patent recycles the spent acid which apparently still contains excess nitric acid and acetic anhydride. Even though the HMX nitrolysis and the RDX nitrolysis employ the same reagents, these processes are very different, since the proportions of reagents, reaction temperatures, reaction mechanisms and precursors and by-product nitramines are significantly different.

BRIEF DESCRIPTION OF THE DRAWING

The drawing shows a flow diagram of a specific embodiment of the RDX nitrolysis process of the present invention.

DETAILED DESCRIPTION OF THE INVENTION

Conventional Process

Referring to the flow diagram of the RDX nitrolysis shown in the drawing, the three feedstreams which are entered into the reactor are as follows:

(1) a solution of 100 g (0.714 moles) hexamine in 164.7 g (2.745 moles) acetic acid,
(2) a solution of 166 g (2.075 moles) ammonium nitrate in 212 g (3.365 moles) nitric acid, and
(3) 575.1 g (5.638 moles) acetic anhydride.

The feed streams were added incrementally over a 15 minute period to an agitated reactor containing a heel maintained at 65° C. and consisting of 35 ml acetic anhydride, 30 ml of nitric acid/ammonium nitrate (56/44) solution, 20 g of ammonium nitrate and 785 ml of acetic acid. Following the addition of the reagents the slurry was aged for 40 minutes at 65° C. to complete the nitrolysis.

Since the nitrolysis reaction requires anhydrous conditions, it is essential to avoid or minimize the presence of water in the spent acid to be recycled. Therefore, to determine the effect of strength of the simmer acid, several nitrolysis batches were carried out in the manner described above except that various amounts of water were added to the aged RDX slurry, which was then heated to 98° C. for 30 minutes to effect the simmering operation. The results are set forth in Table I, which shows that there is a decrease of about 6% in yield of RDX due to solubility of the RDX in the stronger acid as the simmer acid concentration is varied from 60% (40% water content), employed in the standard process, to 100%. (0% water content).

Conventional Process Modified According to the Present Invention

The following examples illustrate specific embodiments of the method of carrying out the process of the present invention under conditions, which permit recycling of spent acid with little, if any, reduction of RDX yield and avoid or minimize the need to process spent acid through the conventional, costly recovery system.

EXAMPLES 1-5

These examples describe experiments, wherein spent acid was initially generated from a virgin batch prepared under the standard process conditions described above except that the simmering step was accomplished in spent acid containing one percent by weight of water, and the spent acid filtrate was recycled in four consecutive batches under the following condition: a portion (264.7 g) of the recycle spent acid containing 1% water was employed to prepare the hexamine solution.

TABLE II

RDX Nitrations Using Acid Recycle and 1% Water in Hexamine Solution

| Example | Assay of Spent Acid | | % HMX | % Comp C | Crude RDX Yield g/g Hexamine | Pure RDX Yield g/g Hexamine |
| | % Nitric Acid | % Acetic Acid | | | | |
|---|---|---|---|---|---|---|
| 1 (virgin batch) | 3.41 | 91.61 | 5.44 | 2.79 | 2.52 | 2.31 |
| 2 | 3.53 | 91.36 | 6.30 | 4.87 | 2.57 | 2.28 |
| 3 | 3.43 | 91.56 | 2.47 | 1.46 | 2.46 | 2.36 |
| 4 | 3.52 | 90.73 | 2.70 | 1.33 | 2.43 | 2.33 |
| 5(a) | 1.55 | 93.09 | 6.84 | 2.52 | 2.42 | 2.19 |

(a)Nitric Acid - ammonium nitrate was reduced 20%

TABLE I

Standard RDX Nitrolyses - Effect of Increased Acid Strength During Simmer

| Batch | % H$_2$O | Assay of Spent Acid | | Crude RDX | | | Pure RDX |
| | | % Nitric Acid | % Acetic Acid | % HMX | % Comp C(2) | Yield g/g Hexamine | Yield g/g Hexamine |
|---|---|---|---|---|---|---|---|
| 1 (Control)(1) | 40 | 1.88 | 59.04 | 4.55 | 0.82 | 2.521 | 2.387 |
| 2 | 30 | 2.20 | 63.93 | 3.34 | 0.88 | 2.467 | 2.362 |
| 3 | 20 | 2.48 | 75.90 | 2.34 | 1.53 | 2.408 | 2.315 |
| 4 | 10 | 2.15 | 83.62 | 0.81 | 1.07 | 2.335 | 2.291 |
| 5 | 1 | 2.95 | 90.00 | 1.45 | 0.89 | 2.318 | 2.264 |
| 6 | 0 | 2.16 | 91.09 | 0.00 | 1.98 | 2.282 | 2.237 |

(1)denotes standard process
(2)Compound C is the trivial name given to the major impurity present in RDX and HMX produced in the process. Compound C is presently unidentified but is probably a methylene nitramine polymer.

With the above exception the nitrolysis conditions were equivalent to the standard process. The reclaimed spent acid from each batch was recycled to the next batch.

The results set forth in Table II show that under the aforementioned recycle conditions, spent acid can be recycled to the process with little, if any reduction in yield of RDX as compared with the RDX yield obtained by the standard process.

In conventional batch nitrolysis of hexamine to RDX, the hexamine is fed to the heel as a concentrated solution in acetic acid. Acetic acid is also used in the nitrolysis heel. The nitric acid-ammonium nitrate solution is normally fed to the reaction medium at a rate to ensure that nitric acid is present at all times. The free nitric acid in the reaction medium is one of the control parameters that can be monitored and is referred to as nitric acid "excess". These nitrolyses are carried out in the presence of acetic anhydride under anhydrous conditions so that water is not inherently present in the spent acid resulting from the nitrolysis.

In carrying out the process of the present invention sufficient water is added to the reaction mixture after completion of the nitrolysis reaction, to eliminate the acetic anhydride present and to provide a slurry liquid of 0% to about 2% water content for the simmer purification step. The simmering purification step can be accomplished by heating the slurry liquid, adjusted to 0-2% water content, to an elevated temperature, preferably about 90°-100° C., until the by-products of the nitrolysis reaction, notably linear nitramines, are destroyed, after which the spent acid can be separated from the solid RDX, e.g. by filtration, and recycled. Larger amounts of water are preferably not incorporated in the recycled spent acid to minimize the amount of acetic anhydride required to make the system anhydrous for the nitrolysis reaction.

The amount of recycle spent acid of 0-2% water content employed to dissolve the hexamine reactant is ordinarily restricted to that which is sufficient to dissolve the hexamine. About 15-20% of the spent acid generated per batch is required to dissolve the hexamine feedstock for a subsequent nitrolysis batch. This amount of spent acid is fixed by requirements of solution composition and is near the minimum amount required to dissolve the hexamine. The use of smaller amounts of spent acid is less preferred, since it would result in incomplete dissolution of the hexamine; while the use of larger amounts of spent acid to dissolve the hexamine is also less preferred, since it would have the adverse effect of increased volume throughout with no RDX yield increase.

When the spent acid from the simmer purification step is recycled to the hexamine feed solution and the nitrolysis heel, the excess nitric acid usually present therein is not neutralized with sodium acetate, or equivalent, to avoid the loss of RDX yield at the expense of increased HMX yield. Spent acid recycled to the nitrolysis heel is mixed with acetic anhydride if necessary, to eliminate any water contained therein so as to provide the anhydride conditions required in the nitrolysis reaction.

Optimum results are obtained when a portion of the recycled spent acid, obtained by simmering at high acid strength (98-99% corresponding to 1-2% water content), is utilized without modification to prepare the hexamine solution (i.e. neither the excess nitric acid nor water content is eliminated), and the remainder of the recycle spent acid is made anhydrous with acetic anhydride and then utilized as the heel, as illustrated in the examples.

The conditions under which the recycling of spent acid is feasible according to the present invention are based on several important discoveries discussed below.

(1) As shown in Table I, it has been found that RDX can be simmered in strong acid in concentrations up to 100% (0% water content) to destroy by-products e.g. linear nitramines, with little or no loss in yield except that due to the greater solubility of the RDX in the more concentrated acid.

(2) It has also been found that the spent acid from the simmering step can be recycled repeatedly without progressive buildup of byproduct nitramines. Table III shows the results of experiments, wherein spent acid was generated initially from a virgin batch prepared under standard conditions and the simmer step was carried out in spent acid containing 1% and 2% water. The spent acid filtrate was used in four consecutive recycles under the following conditions:

a. The recycle acid was used to dissolve hexamine (264.7 g acid per 100 g hexamine). Acetic anhydride was added to the recycle acid sufficient to restore anhydrous conditions i.e. no excess anhydride was used, prior to hexamine dissolution.

b. The heel was standard in composition and volume. Spent acid was not recycled to the heel.

c. With the above exceptions, the nitrolysis conditions were equivalent to the standard process conditions described above. Reclaimed spent acid from each batch was recycled to the next batch.

(3) It has also been found that the reaction product formed beween hexamine and the recycle spent acid employed to prepare the hexamine feedstock solution is quite dependent on the water content of the spent acid and in turn has an important effect on the yield of RDX produced. Thus, for example, a. When the hexamine feedstock solutions were prepared with recycled spent acid containing 1% water and normal (about 2%) nitric acid excess, using 264.7 g spent acid per 100 g hexamine, and the remainder of the spent acid was recycled to the heel after first removing its water content by addition of acetic anhydride, as described in Examples 1-5, the following results were obtained:

(1) The nitric acid in the recycled spent acid reacted with hexamine to form hexamine mononitrate, leaving no free nitric acid in the solution. About 12% of the hexamine reacted in the mixing step.

(2) The RDX yields were only about 1% lower than control batches due to greater volume and solubility.

b. When the hexamine solutions were prepared with recycled spent acid containing 1% acetic anhydride and normal (about 2%) nitric acid excesses and using standard heel conditions (composition and volume), the following results were obtained:

(1) 1-acetamidomethylhexamine1-nitrate was formed and remained in solution, leaving no free nitric acid in the solution. About 20% of the hexamine reacted during the mixing step.

(2) The RDX yields obtained in the RDX nitrolysis batches were about 23% lower than control batches due to the formation of larger amounts of HMX. Since 1-acetamidomethylhexamine-1-nitrate has been shown to nitrolyze to a product rich in HMX, its presence may possibly explain the smaller RDX yields and greater amounts of HMX obtained.

c. When the hexamine solutions were prepared with recycled spent acid, wherein the normal nitric acid excess was removed by neutralization with sodium acetate, two conditions were investigated:

(a) The neutralized recycle acid was used only for preparing the hexamine solution and standard heel conditions (composition and volume) were employed, i.e. the neutralized acid was not recycled to the heel.

(b) The neutralized recycle acid was used for preparing the hexamine solution and also as a nitrolysis heel.

As shown in Table IV, recycle of the neutralized spent acid to both the hexamine feed and the heel resulted in a large increase in yield of HMX produced at the expense of RDX yield, but not when it was recycled only to the hexamine feed. Thus, the average HMX content of the crude product progressed from 2.28% (for spent acid-hexamine solution) to 5.06% (standard) and the 23.86% (recycle to both hexamine feed and nitrolysis heel). This result is of potential interest for simultaneous production of RDX and HMX from a single nitrolysis reaction and at RDX economics. The economics involve a trade-off between RDX losses, HMX gains and the use of a single nitrolysis system rather than separate facilities, as in current practice.

The foregoing disclosure and drawings are merely illustrative of the principles of this invention and are not to be interpreted in a limiting sense. We wish it to be understood that we do not desire to be limited to the exact details of construction shown and described, because obvious modifications will occur to a person skilled in the art.

TABLE III

| | RDX Nitrolyses - Strong Acid Simmer and Recycle | | | | | | |
|---|---|---|---|---|---|---|---|
| | Assay of Spent Acid | | | Crude RDX | | Pure RDX | Batch from which |
| Batch | % Nitric Acid | % Acetic Acid | % HMX | % Comp C | Yield g/g Hexamine | Yield g/g Hexamine | Acid was Recycled |
| 1[a] | 2.99 | 91.26 | 0.89 | 1.55 | 2.50 | 2.44 | Virgin batch |
| 2[a] | 3.96 | 91.21 | 0.00 | 0.34 | 1.91 | 1.90 | 1 |
| 3[b] | 3.57 | 87.81 | 3.10 | 0.40 | 1.98 | 1.91 | 2 |
| 4[b] | 3.59 | 90.89 | 1.20 | 1.40 | 1.93 | 1.88 | 3 |
| 5[b] | 1.87 | 91.90 | 4.90 | 1.25 | 1.91 | 1.79 | 4 |

[a]Simmered in spent acid adjusted to 1% water content by addition of water.
[b]Simmered in spent acid adjusted to 2% water content by addition of water.
Byproduct linear nitramines were not detected in any of the recycled spent acids by thin layer chromatography (TLC) and gas liquid chromatography (GLC) techniques.

TABLE IV

RDX Nitrolyses Using Acid Recycle With Nitric Acid Content Neutralized

| | Assay of Spent Acid | | Crude RDX | | | Pure RDX | |
| --- | --- | --- | --- | --- | --- | --- | --- |
| Batch | % Nitric Acid | % Acetic Acid | % HMX | % Comp C | Yield g/g Hexamine | Yield g/g Hexamine | Batch from Which Acid was Recycled |
| 1 | 1.53 | 93.53 | 3.92 | 2.19 | 2.49 | 2.34 | Virgin Batch |
| 2(a) | 3.29 | 87.23 | 22.42 | 1.92 | 2.00 | 1.51 | 1 |
| 3(a) | 3.05 | 86.67 | 25.30 | 2.16 | 2.05 | 1.49 | 2 |
| 4 | 3.26 | 92.28 | 6.20 | 1.44 | 2.54 | 2.35 | Virgin Batch |
| 5(b) | 3.73 | 87.98 | 2.25 | 1.52 | 2.03 | 1.95 | 4 |
| 6(b) | 3.93 | 90.92 | 2.30 | 1.68 | 2.04 | 1.96 | 5 |

(a)Acid was recycled to both the heel and the hexamine solution
(b)Acid was recycled only to the hexamine solution

We claim:

1. A process for producing 1,3,5-trinitro-1,3,5-triazacyclohexane, by nitrolysis of hexamine, which comprises:
   (a) introducing a solution of hexamine in acetic acid, a solution of ammonium nitrate in nitric acid, and acetic anhydride in stoichiometric excess over the proportions required to form 1,3,5-trinitro-1,3,5-triazacyclohexane, into a heel consisting essentially of acetic acid;
   (b) heating the mixture under anhydrous conditions to effect nitrolysis and production of 1,3,5-trinitro-1,3,5-triazacyclohexane and a spent acid containing acetic acid, acetic anhydride, and nitric acid;
   (c) adding water to said spent acid- 1,3,5-trinitro-1,3,5-triazacyclohexane mixture sufficient to eliminate the acetic anhydride contained therein and adjust the water content of between 0% and about 2%;
   (d) simmering the mixture to destroy linear nitramines;
   (e) separating the 1,3,5-trinitro-1,3,5-triazacyclohexane from the spent acid; and
   (f) recycling at least part of said spent acid containing nitric acid and 0-2% water to dissolve the hexamine reactant.

2. The process of claim 1, wherein a part of the spent acid, after elimination of any water content with acetic anhydride, is recycled to the heel.

3. The process of claim 1, wherein the recycle spent acid used to dissolve hexamine contains about 1% water.

4. The process of claim 1, wherein about 15–20% of the recycle spent acid is employed to dissolve the hexamine.

5. The process of claim 1, wherein the spent acid is neutralized to remove the nitric acid content thereof and recycled to the heel as well as to dissolve the hexamine reactant, whereby a 1,3,5-trinitro-1,3,5-triazacyclohexane product containing an increased content of 1,3,5,7-tetranitro-1,3,5,7-tetraazacyclooctane is obtained.

6. The process of claim 5, wherein the spent acid is neutralized with sodium acetate.

* * * * *